United States Patent [19]

Folkard et al.

[11] Patent Number: 5,061,072
[45] Date of Patent: Oct. 29, 1991

[54] DIFFERENTIAL ELLIPSOMETER

[75] Inventors: Margaret A. Folkard, Kensington Park; Richard H. Hartley, Seaview Downs, both of Australia

[73] Assignee: c/o The Secretary, Comonwealth of Australia Department of Defence, Canberra, Australia

[21] Appl. No.: 416,311

[22] PCT Filed: Jan. 10, 1989

[86] PCT No.: PCT/AU89/00009
§ 371 Date: Oct. 31, 1989
§ 102(e) Date: Oct. 31, 1989

[87] PCT Pub. No.: WO89/06354
PCT Pub. Date: Jul. 13, 1989

[30] Foreign Application Priority Data

Jan. 11, 1988 [AU] Australia ................ PI6249

[51] Int. Cl.$^5$ ............................. G01N 21/21
[52] U.S. Cl. ...................................... 356/369
[58] Field of Search .......................... 356/369

[56] References Cited
U.S. PATENT DOCUMENTS
4,655,595 4/1987 Bjork et al. .

FOREIGN PATENT DOCUMENTS
61951 3/1987 Australia .
102470 3/1984 European Pat. Off. .

OTHER PUBLICATIONS

Smith, "An Automated Scanning Ellipsometer", Surface Science, vol. 56, No. 1, pp. 212-220, 6/76.
Derwent Abstract Accession No. 87-269624/38, Class S03, SU,A, 1288558 (USSR RADIO ELTRN) Feb. 7, 1987.
Derwent Abstract Accession No. 86-3111148/47, Class S02,SU,A1226042 (Optical Society of America, New York), R. M. A. Azzam, 'Simple and Direct Determination of Complex Refractive Index and Thickness of Unsupported or Embedded Thin Films by Combined Reflection and Transmission Ellipsometry of 45° angle of Incidence',see pp. 1080-1082.

Primary Examiner—Davis L. Willis
Assistant Examiner—Matthew W. Koren
Attorney, Agent, or Firm—Cushman, Darby & Cushman

[57] ABSTRACT

A differential ellipsometer to measure the epitaxial growth of crystalization materials by molecular beam epitaxy. The ellipsometer projects a light beam (3) to the surface, and the reflected light beam (5) is returned to another point on the surface with the P and s linear polarization states interchanged. The output beam (7) from the further point is brought into interference with part of the incident beam for measurement or analysis.

6 Claims, 3 Drawing Sheets

DIFFERENTIAL ELLIPSOMETER

This invention relates to a differential ellipsometer, more particularly to an ellipsometer for measuring differences in the ratio of complex amplitude reflectance (or the effective complex refractive index) between two or more regions of a sample. The differential ellipsometer may be used in either a transmission or a reflection mode.

BACKGROUND OF THE INVENTION

Ellipsometry is used to determine the state of polarisation of light. When a polarised light beam interacts with an optical system, the polarisation state of the beam may be modified by the optical system. By careful measurements of the initial and final states of polarisation, properties of the optical system under study may be obtained. This is the general use of ellipsometry. Of special relevance to this invention is the use of ellipsometry for measuring the effective complex refractive index of a small region of a sample.

For the conditions that prevail during the epitaxial growth of crystalline materials by molecular beam epitaxy, the crystal surface is clean and unaffected by oxides and other contaminating layers. Under these conditions it is possible to measure the optical properties of the material without the complicating effects of contaminants. In addition for many materials the refractive index varies with the proportion of constituent components and it is therefore possible to use ellipsometry to measure the composition of the material. This may be very useful in the case of the molecular beam epitaxial growth of compounds. The low energy gap semiconducting material cadmium mercury telluride ($Cd_xHg_{1-x}Te$) is such a material. Here 'x' is the molar fraction of cadmium telluride in the alloy.

Cadmium mercury telluride for use in infrared optoelectronic devices is prepared in the form of very thin single crystal layers. The composition required for the layers is determined by the portion of the infrared spectrum in which the devices are intended to operate. In order that device production yields be economically viable it is important that the composition of the layers be controlled to a high level of uniformity across the area over which devices are to be made. A variety of epitaxial growth methods are employed to grow single crystal layers of cadmium mercury telluride. All methods known to us produce thin films with variations in composition larger than 0.001 in the molar fraction of cadmium telluride across a distance of approximately 2 centimeters.

DESCRIPTION OF THE PRIOR ART

A method of controlling the compositional uniformity of epitaxial layers is the subject of Australian Patent Application No. 6195186. In the said application an ellipsometer may provide information on the composition at a point on the surface of the film. This information may in turn be used in a closed loop system to control the composition of the growing film at that point. By a variety of possible means, such as scanning the ellipsometer beam across the film, the composition of the film at any number of points may be monitored and hence controlled and the uniformity of the film assured.

In the growth method of said patent application if the compositional information is obtained by ellipsometry, then for each point on the film for which the composition is to be controlled it is necessary to perform one fourier transform per sample period. To obtain the necessary precision of measurement the fourier transform must use a large number of sampled data. Such transforms are time consuming to compute, and may limit the number of points which can be monitored on the film or the frequency with which they can be monitored. In the case of the epitaxial growth of cadmium mercury telluride by molecular beam epitaxy, a fourier transform using at least 1024 sampled data, must be carried out each second for every point of interest on the film. This could require many thousands of transforms to be carried out each second. The computing power required to achieve this level of performance is very costly and it is therefore desirable to reduce the number and complexity of the calculations necessary to obtain the composition information across the film surface.

For small variations in composition across the surface of the film, differential measurement techniques may be used. These difference values may be converted to absolute values provided at least one of the points is measured absolutely. For any given accuracy of the end result required, the differential measurements may be made with a lower precision than absolute measurements. Accordingly the differential measurements may use fourier transforms of smaller numbers of sampled data. Because the computing time for a fast fourier transform is approximately proportional to the number of data values transformed, a reduction in the number of data values needed, decreases the computing time by the same proportion. Using this differential method, considerable savings in computing time may be achieved.

Patent No. SU1226-042-A is directed to the measuring of film thickness on a substrate by using an ellipsometer for biaxial refraction pattern measurements on bare, coated and alternating-patch specimens. The film thickness is given by a formula related to wave length, incident angle, and a parameter derived from Fresnel coefficients.

Patent No. SU1288-558-A is a materials ellipsometric measurement by changing polarisation azimuth within two bands and noting signal minima values.

European Patent Application Publication No. 0102470 is an ellipsometric measuring system to measure the thickness of film deposited in a furnace. A plurality of substrates are positioned in the furnace and a laser beam is reflected from one substrate to another and then to a receiver unit outside the furnace.

Publication entitled "Simple and Direct Determination of Complex Refractive Index and Thickness of Unsupported or Imbedded thin films by Combined Reflection and Transmission Ellipsometry at 45° Angle of Incidence" by R. M. A. Azzam in The Journal of Optical Society of America, (Volume 73, No. 8/Aug. '83, Pages 1080, 1081 and 1082) discusses a direct determination of the complex refractive index and thickness of an absorbing thin film that is bounded on both sides of transparent media of the same known refractive index.

It is an object of this invention to provide differential measurements of the complex ratio of amplitude reflectance between two or more points on a surface, while providing the absolute measurement of the complex ratio of amplitude reflectance for at least one point.

BRIEF STATEMENT OF THE INVENTION

Thus there is provided according to the invention a method of measuring the growth on a surface comprising the steps of reflecting a light beam from the surface, scanning or expanding the light beam across the surface, and comprising the steps of comparing the ellipsometric information on the beam obtained from one area of the surface (the reference point), with the ellipsometric information on the light beam from other points on the surface.

BRIEF DESCRIPTION OF THE DRAWINGS

In order to more fully describe the invention reference will be made to the accompanying drawings in which.

DESCRIPTION OF THE PREFERRED EMBODIMENT

Figure 1:
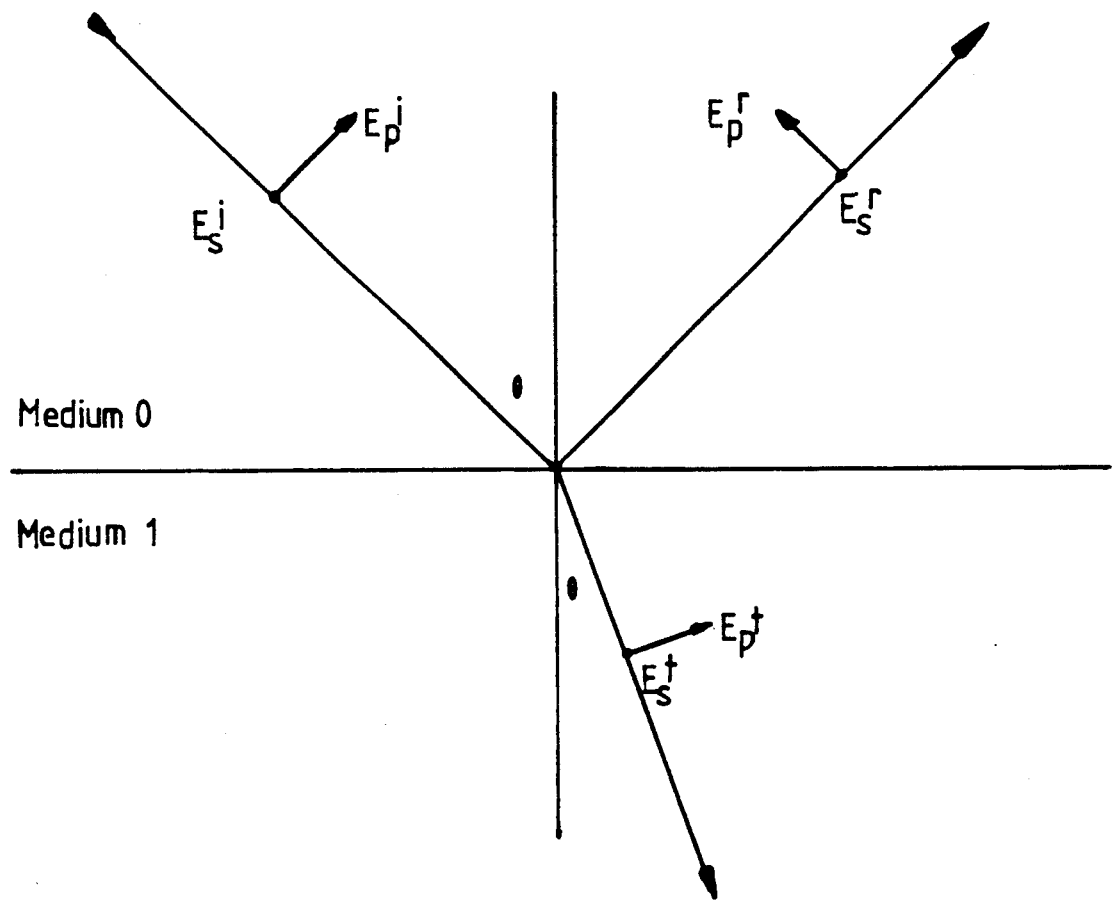
FIG. 1 is a schematic illustration of an incident and reflected beam.
Figure 2:
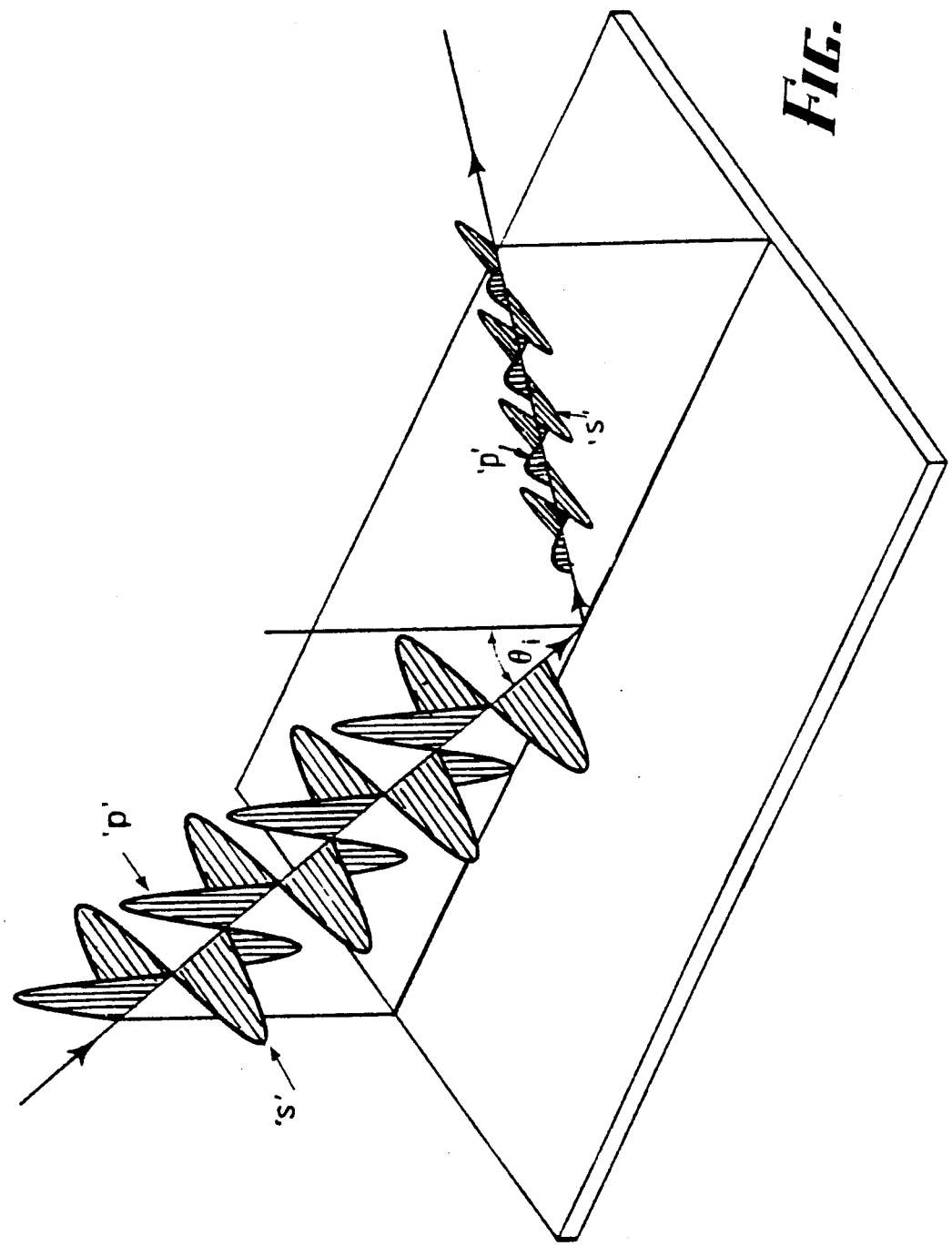
FIG. 2 is a schematic illustration of the "p" and "s" components of an incident and reflected light beam.

Any incident light wave can be considered as the sum of two independent components whose electric field vectors $E_p$ and $E_s$ vibrate parallel (p) or perpendicular (s) to the plane of incidence. Interaction with a surface affects the 'p' and 's' components quite differently, as is indicated schematically in FIG. 1. This is shown more clearly in FIG. 2, where the input beam is linearly polarised with its p and s components equal in phase and amplitude. After reflection the amplitudes of the p and s components of the output beam are no longer equal, and there is a phase difference between them.

An ellipsometric measurement determines the complex amplitude reflectance ratio $\rho$. When the incident p and s components are of equal amplitude, then $\rho = r_p/r_s$, where $r_p$ and $r_s$ are the complex amplitudes of the individual p and s components of the reflected beam.

$$r_p = \frac{E_{pr}}{E_{pi}} = |r_p| e^{i\delta_p}$$

$$r_s = \frac{E_{sr}}{E_{si}} = |r_s| e^{i(\delta_p - \delta_s)}$$

$$\rho = \frac{r_p}{r_s} = \frac{|r_p|}{|r_s|} e^{i(\delta_p - \delta_s)}$$

$$\rho = \tan\psi \exp(i\Delta).$$

Thus $$\tan\psi = r_p/r_s$$

and $$\Delta = \delta_p - \delta_s.$$

Tan $\psi$ is the change in the ratio of the amplitudes introduced by the reflection, and $\Delta$ is the phase difference between the reflected p and s components. The individual p and s phase shifts $\delta_p$ and $\delta_s$ can be measured only with great difficulty, however their difference $\Delta$ may be readily determined.

Figure 3:
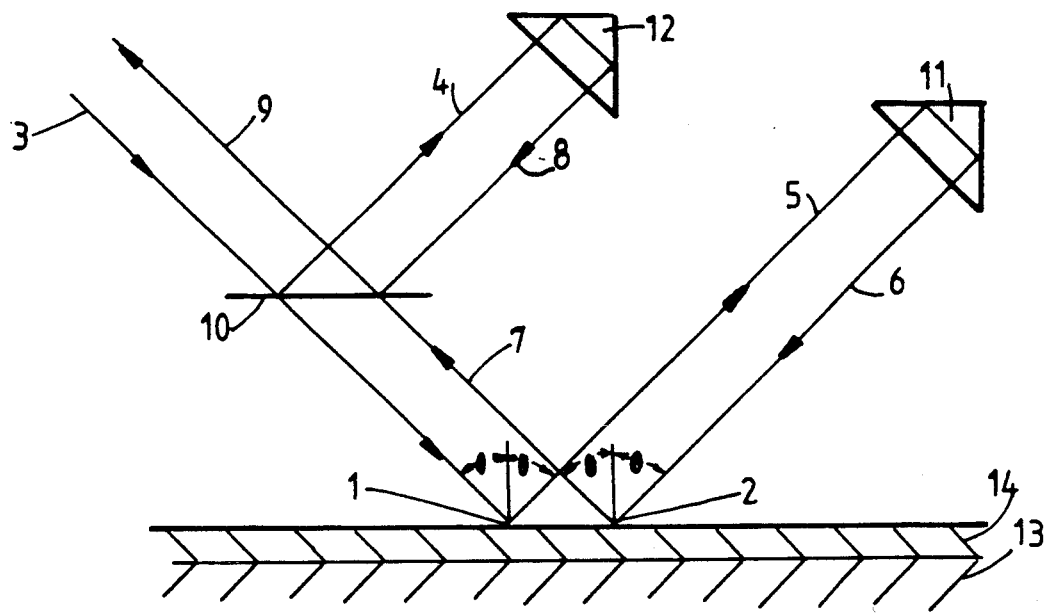
FIG. 3 is a diagram showing the relationship of the ellipsometry measurement beams in relation to the film being deposited on the substrate.

Referring to FIG. 3, the substrate 13 has on it a film 14 on to which a light beam 15 is directed at an angle of incidence $\theta$ and is reflected from the film from reference point 1 onto an optical component 11 chosen to return the beam of light to a second point 2 on the film at the same angle of incidence $\theta$ and with the p and s linear polarisation states interchanged. If the effective complex refractive index at each of the two points on the film is the same, the polarisation state of the beam after reflection from the two points will be the same as the polarisation state of the beam before reflection. If the effective complex refractive indices at the two points of the film are only approximately the same, then the change in polarisation state of the beam contains the difference information that is sought, but the net change in polarisation state of the beam is only apparent by comparing the polarisation states before and after the reflections. By causing the output beam 7 to be brought into interference with part of the input beam 3 (via beam splitter 10 and optical component 12 via paths 4 and 8), information related to this net change in polarisation state may be placed on a single beam 9 for measurement and analysis.

The method also relates to the manner in which the differential information is obtained from the final output beam 9. The ratio of the complex reflectivities for the p and s polarisations is normally referred to as $\rho$ i.e. ($\rho = r_p/r_s$). $\rho$ completely specifies the effective complex refractive index and hence to obtain high accuracy differential information from the final output beam 9 it is sufficient to measure differential changes in $\rho$. Since $\rho$ is complex, two differences are needed, for example one of phase and one of magnitude is suitable, but clearly there are other possible choices.

Figure 4:
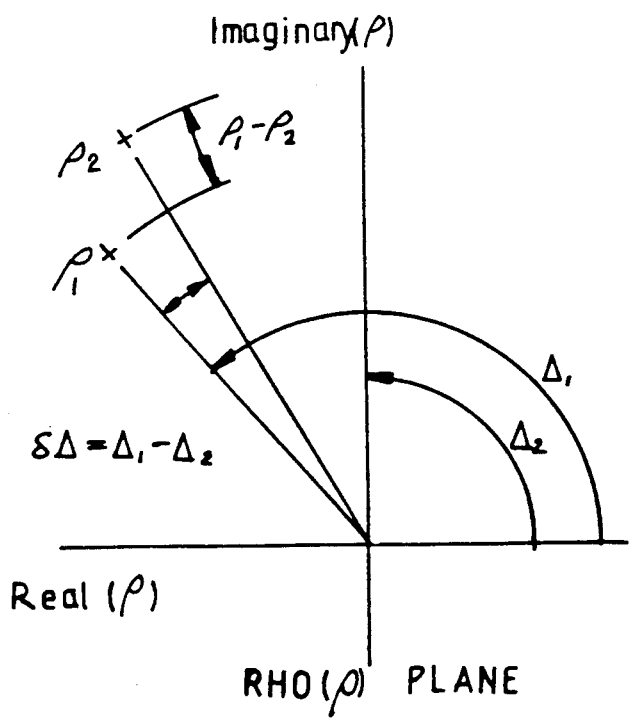
FIG. 4 is an illustration of the principle of measurement.

FIG. 4 is a schematic view showing the principle of measurement as described. $\rho_1$ is measured at point 1, the reference point, while $\rho_2$ is measured at point 2, the other point. The differential measure of phase is shown as $\delta\Delta$ and the differential magnitude may be taken as $|\rho_1| - |\rho_2|$ which is equivalent to $(|r_p1| \ |r_s2| - |r_p2| \ |r_s1|)/|r_s1| \ |r_s2|$. The measurement performed by the ellipsometer is truly differential, and this is achieved by arranging to measure $(|r_p1| \ |r_s2| - |r_p2| \ |r_s1|)/|r_s1| \ |r_s2|$ and $\delta\Delta$ directly from the ellipsometer.

Thus with the invention the area is covered by selecting a reference point to be measured with high precision, and scanning other points to measure the difference in $\rho$ between the further points and the reference point. The difference between the reference point and the other points may be gained either by scanning, or by beam expansion methods. This difference information is obtained by the action of interchanging the p and s polarisation states between reflections from the reference point and the measurement point. Thus with this invention there is the capacity to measure with high precision the uniformity of refractive index over an area of a few square centimeters in times of the order of one second.

The differential information needed, may be separated from the final output beam 9 by a number of methods, these include all or some of the following; phase modulation of beam 3, phase modulation of beam 8 and frequency shifting of beam 4. After detection of the final output beam 9 with a suitable photodetector, a spectrum analysis may be performed by any suitable means (such as sampling and fourier transform) and the coefficients of the appropriate frequency components yield both the differential information and the absolute information for the reference point.

The differential ellipsometric information on the beam is obtained by exchanging the p and s polarisation states in between reflections from the reference and secondary point. The phase and magnitude changes imparted to the beam by the reference area are approximately cancelled by the changes imparted by the secondary area. This same sort of comparison may be carried out for many secondary areas simultaneously by ensuring that the beam interacting with the secondary regions is beam expanded with respect to the small beam diameter at the reference area. This change of beam diameter may be carried out, for example, using lenses with sufficiently large focal lengths to minimize changes of polarisation states of the light.

Examples of interferometric ellipsometers are to be found in the literature (Hazebroek and Holscher J. Phys. E: Sci. Instr. 6, 822 [1973]). These do not however attempt to measure differential quantities. There are however examples of differential ellipsometers in the literature (T. Sandstrom; Journal de Physique, Colloque C10, Supplement No. 12, TOME 44, December 1983) but these are not fully differential.

Although one form of the invention has been described in some detail it is to be realised that the invention is not limited thereto but can include various modifications fully within the spirit and scope of the invention.

We claim:

1. A method for measuring epitaxial growth on a surface, comprising the steps of:

reflecting an incident light beam from the surface;
   scanning or expanding said light beam across said surface;
   comparing ellipsometric information on said light beam obtained from a reference point area of said surface with ellipsometric information on said light beam from a plurality of other points on said surface, to directly obtain differential measurement between said reference point area and each of said other points.

2. A method as defined in claim 1 wherein the light beam reflected from the surface is returned to a further point on the surface with the same angle of incidence with the p and s linear polarisation states interchanged.

3. A method as defined in claim 2 wherein the incident light beam and the beam reflected from the further point pass through a beam splitter, the incident beam from the beam splitter being returned to the beam splitter so that output light beam from the further point is brought into interference with part of the input beam.

4. A differential ellipsometer for measuring the epitaxial growth on a surface, said ellipsometer comprising means for projecting a light beam on to a point of the surface, means for returning the reflected beam to a further point on the surface with p and s linear polarisation states interchanged, and further means causing the output beam reflected from the further point to be brought into interference with part of the incident beam for measurement or analysis.

5. A differential ellipsometer as defined in claim 4 wherein means for returning the reflected beam comprises a prism.

6. A differential ellipsometer as defined in claim 4 wherein said further means comprises a beam splitter, that portion of the incident beam split from the incident beam being returned by a prism to the beam splitter to be brought into interference with the output beam.

* * * * *